United States Patent [19]

Hamazaki et al.

[11] 4,153,724
[45] May 8, 1979

[54] BENZOYL PHENOXY ACETIC ACID DERIVATIVES

[75] Inventors: Yasuhiko Hamazaki; Toshiyuki Yamamoto, both of Tokyo; Shozo Kawabata, Kami-Fukuoka; Kenji Seri, Tokyo; Masao Sakasai, Tokyo; Reiko Sato, Tokyo; Nobuo Ishiyama, Tokyo, all of Japan

[73] Assignee: Kaken Chemical Co., Ltd., Tokyo, Japan

[21] Appl. No.: 860,478

[22] Filed: Dec. 14, 1977

[30] Foreign Application Priority Data

Dec. 27, 1976 [JP] Japan .................................. 51/156256
Aug. 8, 1977 [JP] Japan .................................. 52/94138

[51] Int. Cl.² .................. C07C 69/95; C07C 65/20; A61K 31/19; A61K 31/215
[52] U.S. Cl. ................................. 424/308; 560/52; 562/460; 424/317
[58] Field of Search ................. 560/52, 62; 562/460; 424/308, 317

[56] References Cited

U.S. PATENT DOCUMENTS 3,914,286 10/1975 Mieville ................................. 560/52

FOREIGN PATENT DOCUMENTS 2003430 9/1970 Fed. Rep. of Germany.
2250327 4/1973 Fed. Rep. of Germany.

*Primary Examiner*—Jane S. Myers
*Attorney, Agent, or Firm*—Oblon, Fisher, Spivak, McClelland & Maier

[57] ABSTRACT

Benzoyl phenoxy acetic acid derivatives having the formula

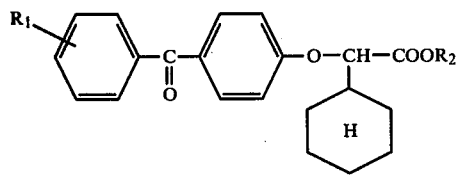

wherein $R_1$ represents hydrogen or halogen atom or a lower alkyl group or a lower alkoxyl group; and $R_2$ represents hydrogen atom or a lower alkyl group which impart excellent antihyperlipidemic activity are provided.

4 Claims, No Drawings

BENZOYL PHENOXY ACETIC ACID DERIVATIVES

BACKGROUND OF THE INVENTION

1. Field of the Invention

The present invention relates to novel benzoyl phenoxy acetic acid derivatives and preparation of the compounds and an antihyperlipidemic agent comprising the compound as the active ingredient.

2. Description of the Prior Art

It has been known to clinically use ethyl-α-(p-chlorophenoxy)-isobutylate and analogous compounds; nicotinic acid derivatives; hormones such as protein assimilation steroids; unsaturated aliphatic acid such as linoleic acid; cholestyamine and β-sitosterols as an antihyperlipidemic agent (D.O.S. No. 2,250,327 and D.O.S. No. 2,003,430).

SUMMARY OF THE INVENTION

It is an object of the present invention to provide novel benzoyl phenoxy acetic acid derivatives which are effective for remedy of hyperlipidemic.

It is the other object of the present invention to provide a process for producing novel benzoyl phenoxy acetic acids.

The foregoing and other objects of the present invention have been attained by providing benzoyl phenoxy acetic acid derivatives having the formula

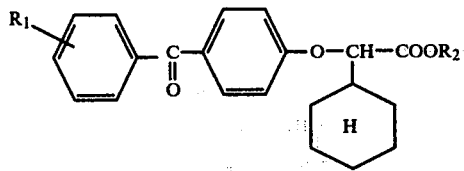

wherein $R_1$ represents hydrogen or halogen atom or a lower alkyl group or a lower alkoxyl group; and $R_2$ represents hydrogen atom or a lower alkyl group which impart excellent antihyperlipidemic activity.

DETAILED DESCRIPTION OF THE PREFERRED EMBODIMENTS

The inventors have studied on the preparations of various benzophenone derivatives and the pharmacological characteristics of the benzophenone derivatives.

As the result, it has been found that the novel benzoyl phenoxy acetic acid derivatives having the formula (I) impart excellent antihyperlipedemic activity. The benzoyl phenoxy acetic acid derivatives (I) also impart excellent anticoagulant and antiinflammatory activities.

In the formula I, $R_1$ is hydrogen atom or halogen atom i.e. -F, -I, -Br or -Cl; a $C_1$-$C_4$ alkyl group or a $C_1$-$C_4$ alkoxy group and $R_2$ is hydrogen atom or a $C_1$-$C_4$ alkyl group especially ethyl group.

The benzoyl phenoxy acetic acid derivatives (I) can be produced by reacting a compound having the formula

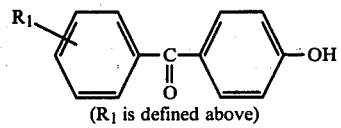

($R_1$ is defined above)

with α-halogenocyclohexyl acetate having the formula

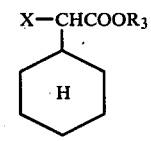

wherein X represents a halogen atom and $R_3$ is a $C_1$-$C_4$ alkyl group; if necessary, hydrolyzing the product.

In the production of the benzoyl phenoxy acetic acid derivative (I), it is preferable to react the compound (II) with the α-halogenocyclohexyl acetate (III) in the presence of a solvent.

The compounds having the formula III wherein X is -I, -Br or -Cl are preferably used. In the reaction, the equimolar amount of α-halogenocyclohexyl acetate (III) is usually reacted with the compound (II). However, it is possible to use excess of either of the compound (II) or the compound (III).

The solvents are organic solvents being inert under the reaction condition such as dimethyl formamide and acetone. The mixed solvent can be used for the reaction.

For example, the reaction can be accelerated by adding a base such as potassium carbonate, sodium carbonate, sodium methylate and sodium ethylate.

It is possible to separate a reaction product obtained by reacting the base with the compound (II), from the reaction system and then, to react the compound (III) with the separated reaction product.

The reaction conditions such as temperature, time and pressure can be decided depending upon the starting materials, the solvent and the base.

The reaction is usually completed at room temperature for 1 to 2 days; or at about 100 to 180° C. for 1 to 6 hours.

The reaction products (I) can be separated and purified by the conventional separating methods such as the concentration; the concentration under a reduced pressure; the distillation; the distillation under a reduced pressure; the fractional distillation; the conversion of alkalinity or acidity; the solvent extraction; the crystallization; the recrystallization; the inversion and the chromatography.

The formulae, boiling points, IR and NMR of typical benzoyl phenoxy acetic acid derivatives (III) are shown in Table 1.

Table 1

| Invention Compound | Formula (I) $R_1$ | $R_2$ | b.p. (°C./mmHg) | IR; $V_{C=O}^{direct}$ cm$^{-1}$ C=O | COOR | NMR δ ppm (in CDCl$_3$) |
|---|---|---|---|---|---|---|
| 1 | p-Cl | Et | 255°–263° C. /0.07–0.09 mmHg 190°–195° C. | 1655 | 1755 | 1.23(t,3H); 1.51–1.91(m,11H); 4.2 (q,2H); 4.44(d,1H); 6.83–7.81(m,8H) 1.20(t,3H); 0.75–2.38(m,11H) |

Table 1-continued

| Invention Compound | Formula (I) R₁ | R₂ | b.p. (°C./mmHg) | IR;V$_{C=O}^{direct}$ cm⁻¹ C=O | COOR | NMR δ ppm (in CDCl₃) |
|---|---|---|---|---|---|---|
| 2 | p-F | Et | /0.27 | 1660 | 1740 | 4.15(q,2H); 4.46(d,1H); 7.80(q,8H) |
| 3 | H | Et | 185°–196° C. /0.5–0.55 | 1660 | 1750 | 1.20(t,3H); 0.82–2.43(m,11H); 4.17(q,2H); 4.48(d,1H); 6.82–7.82(m,9H) |
| 4 | p-OCH₃ | Et | 250°–259° C. /0.25–0.3 | 1660 | 1740 | 1.22(t,3H); 0.75–2.31(m,11H); 3.81(s,3H); 4.18(q,2H); 4.44(d,1H); 7.31(q,8H) |
| 5 | m-F | Et | 190°–195° C. /0.45 | 1660 | 1750 | 1.21(t,3H); 0.93–2.33(m,11H); 4.19(q,2H); 4.49(d,1H); 6.83–7.79(m,8H) |
| 6 | o-F | Et | 190°–200° C. /1 | 1665 | 1750 | 1.18(t,3H); 0.84–2.38(m,11H); 4.14(q,2H); 4.25(d,1H) 6.79–7.83(m,8H) |
| 7 | m-Cl | Et | 215°–220° C. /0.35 | 1665 | 1750 | 1.21(t,3H); 0.88–2.28(m,11H); 4.38(q,2H); 4.44(d,1H); 6.82–7.80(m,8H) |
| 8 | o-Cl | Et | 200°–210° C. /0.16–0.22 | 1670 | 1750 | 1.18(t,3H); 0.96–2.36(m,11H); 4.16(q,2H); 4.46(d,1H); 6.79–7.81(m,8H) |
| 9 | p-CH₃ | Et | 190°–195° C. /0.45–0.6 | 1660 | 1750 | 1.17(t,3H); 0.84–2.44(m,11H); 2.32(s,3H); 4.14(q,2H); 4.48(d,1H); 6.81–7.78(m,8H) |
| 10 | m-CH₃ | Et | 203–213° C. /0.45–0.5 | 1660 | 1750 | 1.22(t,3H); 0.81–2.35(m,11H); 2.37(s,3H); 4.19(q,2H); 4.49(d,1H); 6.82–7.83(m,8H) |
| 11 | o-CH₃ | Et | 195°–197° C. /0.15 | 1660 | 1750 | 1.19(t,3H); 0.79–2.38(m,11H); 2.25(s,3H); 4.15(q,2H); 4.45(d,1H); 6.77–7.78(m,8H) |
| 12 | p-Cl | H | m.p. 130.5°–131.5° C. | **1660 **KBr | 1755 | 0.99–2.31(m,11H); 4.51(d,1H); 6.84–7.84(m,8H); 9.46(broad 1H) |

The inventors have also found that the benzoyl phenoxy acetic acid derivatives having the formula

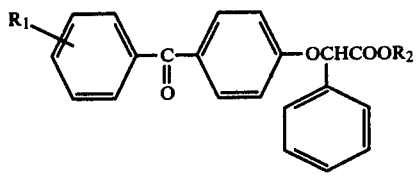

(IV)

wherein R₁ represents hydrogen or halogen atom or a lower alkyl group or a lower alkoxyl group and R₂ represents hydrogen atom or a lower alkyl group also impart antihyperlipidemic activity though the effects are inferior to those of the benzoyl phenoxy acetic acid derivative having the formula (I).

Accordingly, the preparations and the characteristics of the reference compounds (IV) will be described as reference.

The benzoyl phenoxy acetic acid derivatives (IV) can be produced by reacting the compound having the formula

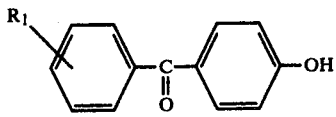

(II)

with an α-halogenophenyl acetate having the formula

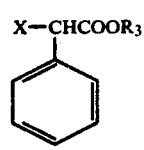

(V)

and if necessary hydrolyzing the products.

The formulae boiling points, IR and NMR of typical benzoyl phenoxy acetic acid.

Table 2

| Reference Compound | Formula IV R₁ | R₂ | b.p. (°C./mmHg) or m.p.*(°C.) | IR:$_{max}^{direct}$ cm⁻¹ C=O | —COOR₂ |
|---|---|---|---|---|---|
| 1 | 2-F | Et | | 1650 | 1750 |
| 2 | " | H | | 1650 | 1740 |
| 3 | 3-F | Et | 235–240/0.175 | 1655 | 1750 |
| 4 | " | H | | 1650 | 1740 |
| 5 | 4-F | Et | 245–250/0.125 | 1650 | 1750 |
| 6 | " | H | | 1640 | 1740 |
| 7 | 2-Cl | Et | 95–97* | 1655* | 1745* |
| 8 | " | H | | 1665 | 1730 |
| 9 | 3-Cl | Et | 99–100* | 1650 | 1745 |
| 10 | " | H | | 1650 | 1730 |
| 11 | 4-Cl | Et | 235–240/.01 | 1650 | 1945 |
| 12 | " | H | | 1650 | 1730 |
| 13 | 2-CH₃ | Et | 109.5–110.5* | 1660 | 1755 |
| 14 | " | H | | 1660 | 1735 |
| 15 | 3-CH₃ | Et | 253–256/0.1 | 1660 | 1755 |
| 16 | " | H | | 1660 | 1735 |
| 17 | 4-CH₃ | Et | 248–251/0.13 | 1660 | 1750 |
| 18 | " | H | | 1655 | 1735 |
| 19 | H | Et | | 1655 | 1745 |
| 20 | " | H | | 1640 | 1730 |

*KBR method; others: nujol method

The above-mentioned conditions of the production of the benzoyl phenoxy acetic acid derivatives (I) can be applied for those of the benzoyl phenoxy acetic acid derivatives (IV).

The novel benzoyl phenoxy acetic acid derivatives (I) impart excellent antihyperlipidemic activity and they are effective as an antihyperlipidemic agent for hyperlipidemia remedy.

The benzoyl phenoxy acetic acid derivatives (I) have low toxicity and they do not cause hepatic disease (hepatitis) which is found by the administration of ethyl-α-(p-chlorophenoxy)-isobutyrate.

The antihyperlipidemic agent of the present invention comprising the benzoyl phenoxy acetic acid derivative (I) can be orally administered in the form of tablet, capsule, powder or granules; and also they can be parenterally administered in the form of injectable, suppository or pellet.

The benzoyl phenoxy acetic acid derivative (I) can be combined with the other antihyperlipidemic agent, a hypotensive agent or an anticoagulant agent.

The dose of the benzoyl phenoxy acetic acid derivative (I) is usually in a range of 50 to 2500 mg preferably 250 to 1000 mg per day per adult in oral dose.

The above-mentioned considerations on the benzoyl phenoxy acetic acid derivatives (I) can be also applied for the reference compounds of benzoyl phenoxy acetic acid derivatives (IV) though the effects of the reference compound (IV) are inferior to those of the compounds (I).

The invention will be further illustrated by certain examples and references.

EXAMPLE 1

Ethyl 2-[p-(4-chlorobenzoyl)-phenoxy]-cyclohexyl acetate having the formula

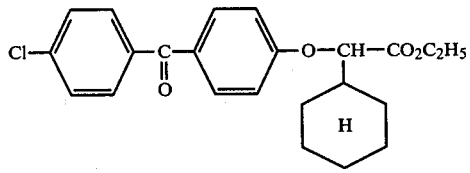

The compound can be produced as follows.

A 5.0 g of 4-chloro-4'-hydroxybenzophenone was dissolved in 20 ml of ethanol and 1.5 g of powdery sodium ethylate was added to the solution and the mixture was concentrated and dried. The dried product was dissolved into 20 ml of dimethyl formamide and 5.5 g of ethyl α-bromocyclohexyl acetate was added and the mixture was heated at 100 to 110° C. for 2 hours and then, dimethyl formamide was distilled off under a reduced pressure. Water was added to the residue and the produce was extracted with benzene and the extract was washed with1% NaOH and then with water and dried with sodium sulfate and the solvent was distilled off. The residual oily product was distilled off under a reduced pressure to obtain 4.3 g (yield of 53.8%) of ethyl 2-[p-(4-chlorobenzoyl)-phenoxy]-cyclohexyl acetate.

IR($V_{C=0}^{direct}$ cm$^{-1}$):1655 (C=0), 1755 (COOC$_2$H$_5$).

NMR (δ ppm, CDCL$_3$): 1.23 (t. 3H); 1.51 to 1.91 (m. 11H); 4.2 (q. 2H); 4.44 (d. 1H); 6.83 to 7.81 (m. 8H).

EXAMPLE 2

Ethyl-2-[p-(4-fluorobenzoyl)-phenoxy]-cyclohexyl acetate having the formula

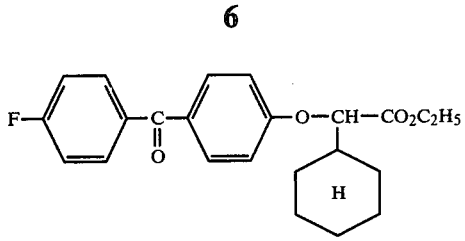

The compound can be produced as follows.

A 5.0 g of 4-fluoro-4'-hydroxybenzophenone was dissolved in 20 ml of ethanol and 1.5 g of powdery sodium ethylate was added and the mixture was concentrated and dried, and then, the dried product was dissolved in 20 ml of dimethyl formamide and 5.75 g of ethyl α-bromocyclohexyl acetate was added and the mixture was heated at 175° to 180° C. for 6 hours and dimethyl formamide was distilled off under a reduced pressure. Water was added to the residue and the product was extracted with benzene and then, the extract was washed with 1% NaOH and then with water and dried with sodium sulfate and the residual oily product was distilled under a reduced pressure to obtain 4.4 g (yield of 50.3%) of ethyl 2-[p-(4-fluorobenzoyl)-phenoxy]-cyclohexyl acetate at a boiling point of 190° to 195° C. (oil bath temp.)/0.27 mmHg.

IR($V_{C=0}^{direct}$ cm$^{-1}$): 1660 (C=0), 1740 (CO$_2$C$_2$H$_5$).

EXAMPLE 3

A 400 g of ethyl 2-[p-4-(chlorobenzoyl)-phenoxy]-cyclohexyl acetate, 400 g of fine powdery silicon dioxide and 185 g of corn starch were uniformly mixed and charged in a kneader and 100 ml of 3% aqueous solution of hydroxypropyl cellulose was added and the mixture was kneaded. The mixture was granulated by passing it through a 16 mesh screen and dried at 50° C. under air current and the product was passed through the 16 mesh screen to form uniform granules which comprise an antihyperlipidemic agent.

EXAMPLE 4

A 400 g of ethyl 2-[p-(4-chlorobenzoyl)-phenoxy]-cyclohexyl acetate, 400 g of lactose and 175 g of potato starch were uniformly mixed and charged into a kneader and 400 ml of 3% aqueous solution of hydroxypropyl cellulose was added and the mixture was kneaded. The mixture was granulated by passing it through a 16 mesh screen and 0.3% of magnesium stearate was added to the granules and the product was compressed to form tablets which comprise an antihyperlipidemic agent.

EXAMPLE 5

Ethyl 2-[p-(3-chlorobenzoyl)-phenoxy]-cyclohexyl acetate having the formula

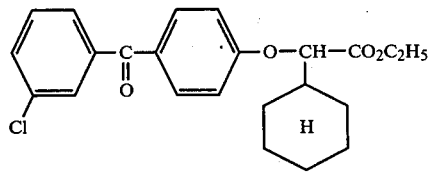

The compound was produced as follows.

A 6.9 g of 3-chloro-4'-hydroxybenzophenone was dissolved in 25 ml of ethanol and 2.0 g of powdery sodium ethylate was added and the mixture was concentrated and dried. The dried product was dissolved in 30 ml of dimethyl formamide and 7.4 g of ethyl α-bromocyclohexyl acetate was added and the mixture was heated at 160° to 170° C. for 8 hours and dimethyl formamide was distilled off under a reduced pressure. Water was added to the residue and the product was extracted with benzene and the extract was washed with 1% NaOH and then, with water and dried with sodium sulfate and the solvent was distilled off. The residual oily product was distilled under a reduced pressure to obtain 3.1 g (yield of 38.8%) of ethyl 2-[p-(3-chlorobenzoyl)-phenoxy]-cyclohexyl acetate at a boiling point of 215° to 220° C. (oil bath temp.)/0.35 mmHg.

EXAMPLE 6

Ethyl 2-[p-(4-methyl benzoyl)-phenoxy]-cyclohexyl acetate having the formula

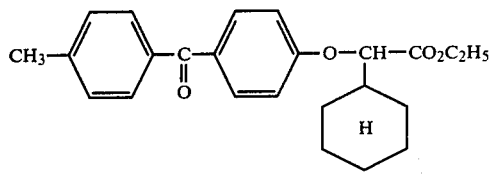

The compound was produced as follows.

A 6.5 g of 4-butyl-4'-hydroxybenzophenone was dissolved in 25 ml of ethanol and 2.0 g of powdery sodium ethylate was added and the mixture was concentrated and dried. The dried product was dissolved in 30 ml of dimethyl formamide and 7.4 g of ethyl α-bromocyclohexyl acetate was added and the mixture was heated at 160° to 170° C. for 6 hours and then, dimethyl formamide was distilled off under a reduced pressure. Water was added to the residue and the product was extracted with benzene and the extract was washed with 1% NaOH and then, with water and dried with sodium sulfate and the solvent was distilled off. The residual oily product was distilled under a reduced pressure to obtain 3.0 g (yield of 42.5%) of ethyl 2-[p-(4-methyl benzoyl)-phenoxy]-cyclohexyl acetate at a boiling point of 190° to 195° C. (oil bath temp.)/0.45 to 0.6 mmHg.

EXAMPLE 7

2-[p-(4-chlorobenzoyl)-phenoxy]-cyclohexyl acetic acid. The compound was produced as follows.

A 1.3 g of ethyl 2-[p-(4-chlorobenzoyl)-phenoxy]-cyclohexyl acetate was added to 10 ml of a potassium hydroxide-ethanol solution (containing 0.54 g of KOH) and the mixture was heated to 35° to 40° C. for 2 hours under stirring and then, ethanol was distilled off under a reduced pressure and benzene was added. The product was extracted with 3% aqueous solution of sodium hydroxide and the extract was acidified with a diluted hydrochloric acid and the product was extracted and the extract was washed with water and dried with sodium sulfate and the solvent was distilled off to obtain a crude crystals. The crude crystals were recrystallized from acetone-n-hexane to obtain 1.15 g (yield of 95.04%) of 2-[p-(4-chlorobenzoyl)-phenoxy]-cyclohexyl acetic acid having a melting point of 130.5° to 131.5° C.

EXAMPLE 8

A 400 g of ethyl 2-[p-3-(chlorobenzoyl)-phenoxy]-cyclohexyl acetate 400 g of fine silicon dioxide and 185 g of corn starch were uniformly mixed and charged in a kneader and 100 ml of 3% aqueous solution of hydroxypropyl cellulose was added and the mixture was kneaded and granulated by passing it through a 16 mesh screen and dried at 50° C. under air current and the product was passed through the 16 mesh screen to form uniform granules which comprise an antihyperlipidemic agent.

EXAMPLE 9

A 400 g of ethyl 2-[p-(3-chlorobenzoyl)-phenoxy]-cyclohexyl acetate, 400 g of lactose and 175 g of potato starch were uniformly mixed and charged in a kneader and 400 ml of 3% aqueous solution of hydroxypropyl cellulose was added and the mixture was kneaded and granulated by passing it through a 16 mesh screen and 0.3% of magnesium stearate was added and the mixture was compressed to form tablets which comprise an antihyperlipidemic agent.

Reference 1

Ethyl 2-[p-(4-chlorobenzoyl)-phenoxy]phenyl acetate having the formula

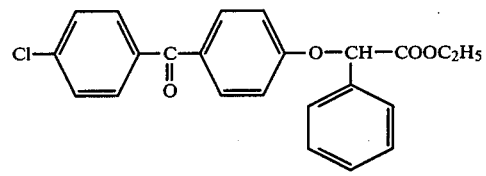

The preparation and the properties of the compound are as follows.

A 7.0 g (0.0302 mole) of 4-chloro-4'-hydroxybenzophenone was dissolved in 40 ml of ethanol and 2.05 g (0.0302 mole) of powdery sodium ethylate was added and the mixture was concentrated and dried.

The dried product was dissolved into 15 ml of dimethyl formamide and 7.3 g (0.0301 mole) of ethyl α-bromophenyl acetate was added and the mixture was heated at 100° C. for 1.5 hours and dimethyl formamide was distilled off under a reduced pressure. Water was added to the residue and the product was extracted with benzene and washed with 2% NaOH and then with water and dried with sodium sulfate and the solvent was distilled off. The remained oily product was passed through a column chromatography with a carrier of Waco Gel C-200 and developed with carbon tetrachloride and then carbon tetrachloride-chloroform mixture to obtain 6.65 g (yield of 55.3%) of ethyl 2-[p-(4-chlorobenzoyl)-phenoxy]phenyl acetate having a boiling point of 235° to 245° C. (oil bath temp. of 0.01 mmHg).

IR ($V_{C=O}^{direct}$ cm$^{-1}$): 1650 (C=O); 1745 (COOC$_2$H$_5$).

NMR (δ ppm CDCl$_3$): CH$_3$ 1.21 (3H, t); CH$_2$=4.19 (2H, q); CH 5.67 (HH. s); arom=6.94 to 7.70 (13H. m).

Reference 2

Ethyl 2-[p-(2-chlorobenzoyl)-phenoxy]phenyl acetate having the formula

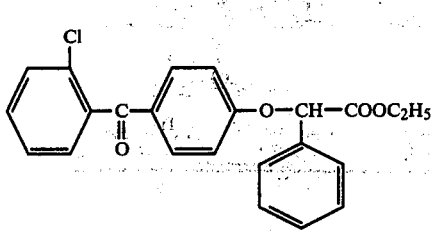

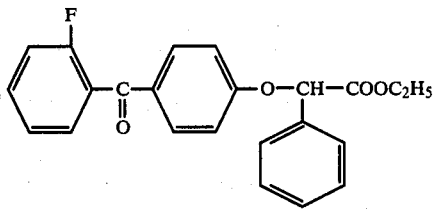

The preparation and the properties of the compound are as follows.

A 7.0 g (0.0302 mole) of 2-chloro-4'-hydroxybenzophenone was dissolved in 40 ml of ethanol and 2.05 g (0.0302 mole) of powdery sodium ethylate was added and the mixture was concentrated and dried. The dried product was dissolved in 15 ml of dimethyl formamide and 7.3 g (0.0301 mole) of ethyl α-bromophenyl acetate was added and the mixture was heated at 100° C. for 1.5 hours.

In accordance with the process of Example 1, the product was treated and recrystallized from methanol-water to obtain 7.3 g (yield of 60.7%) of ethyl 2-[p-(2-chlorobenzoyl phenoxy]phenyl acetate having a melting point of 95° to 97° C.

IR ($V_{C=O}^{KBr}$ cm$^{-1}$): 1655 (C=O); 1745 (COOC$_2$H$_5$).

NMR (δ ppm CDCl$_3$): CH$_3$ 1.19 (3H. t); CH$_3$ 4.18 (2H. q); CH 5.65 (1H. s); arom 6.90 to 7.78 (13H. m).

Reference 3

2-[P-(2-methylbenzoyl)-phenoxy]phenyl acetic acid having the formula

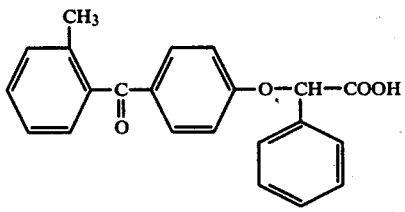

The preparation and properties of the compound are as follows.

3.78 g (0.01 mole) of ethyl 2-[p-(2-methylbenzoyl)-phenoxy] phenyl acetate was added to 30 ml of potassium hydroxide-ethanol solution (containing 1.1 g of KOH) and the mixture was heated at 35° to 40° C. for 1.5 hour under stirring and ethanol was distilled off under a reduced pressure and benzene was added. The product was extracted with 3% aqueous solution of sodium hydroxide and the extract was acidified with hydrochloric acid and the product was extracted with benzene and washed with water and dried with sodium sulfate and the solvent was distilled off to obtain 3.05 g (yield of 79.5%) of 2-[p-(2-methylbenzoyl)-phenoxy]-phenyl acetic acid.

IR ($V_{C=O}^{direct}$ cm$^{-1}$): 1660 (C=O); 1735 (COOH).

NMR (δ ppm CDCl$_3$): CH$_3$ 2.3(3H. s), CH 5.7 (1H, 2), arom 6.98 to 7.75 (13H. m), COOH 10.18 (1H. s).

Reference 4

A 400 g of the compound having the formula 400 g of fine powdery silicon dioxide and 185 g of corn starch were uniformly mixed and charged in a kneader and 3% aqueous solution of hydroxypropyl cellulose was added and the mixture was kneaded. The mixture was granulated by passing it through a 16 mesh screen and dried at 50° C. under air current and the product was passed through the 16 mesh screen to form uniform granules which comprise an antihyperlipidemic agent.

Reference 5

A 400 g of the compound having the formula

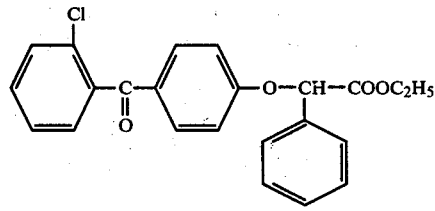

400 of lactose and 175 g of potato starch were uniformly mixed and charged in a kneader and 3% aqueous solution of hydroxypropyl cellulose was added and the mixture was kneaded and granulated by passing through a 16 mesh screen and 0.3% of magnesium stearate was added and the mixture was compressed to form tablets which comprise an antihyperlipidemic agent.

Test 1

The hypolipidemic activity in normal mice (lowering effect of normal blood lipid level).

In the tests, ICR type male mice (weight: about 35 g) were used in groups of 6 each.

Each active ingredient was suspended in a 1% aqueous solution of Tween-80 (polyoxyethylene sorbitane monoalkylate) (Atlas Co.) and the suspension was orally administrated in a dose of 200 mg/Kg.

After 24 hours from the administration, blood was sampled and the concentration of total cholesterols in blood-plasma was measured by the method described in Clinical chemistry Vol. 22 page 393 (1968) and the concentraton of triglyceride (neutral fat) was measured by Fletcher method (Clinica Chimica Acta) Vol. 10 page 451 (1964).

The results are shown in Table 3.

As the active ingredients, the compounds (I) and ethyl-α-(p-chlorophenoxy)-isobutylate having the formula

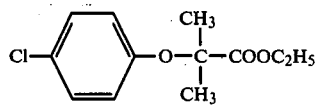

were used.

Test 2

The antihyperlipidemic activity in rats with dietary hyperlipidemia.

In the tests, Wister type male rats (weight: 140 g) were used in groups of 6 each.

A feed containing 2% of cholesterol, 1% of sodium cholate and 5% of cocconut oil was given for 4 days to cause hyperlipidemia.

Each active ingredient was suspended in a 1% aqueous solution of Tween 80 and the suspension was orally administrated in a dose of 100 mg/Kg or 200 mg/Kg once daily for 4 days starting with the supply of the cholesterol supplemented diet.

After 24 hours from the final administration, blood was sampled and the concentration of total cholesterols and the concentration of triglyceride were measured by the methods of Test 1. The results are shown in Table 3.

Test 3

In the acute toxicity tests, male mice (weight: 22 to 25 g) were used in groups of 10 each.

Eash active ingredient was dissolved in olive oil and the solution was orally administrated in a volume corresponding to the body weight.

$LD_{50}$ was calculated by the area method from the mortal percent after 72 hours from the administration. The results are also shown in Table 3.

The compound numbers are the same with those of Tables 1 and 2.

Table 3

| Invention Compound | Rats with hyperlipidemia 200 mg/kg 4 days adm. | | Normal mice(hyplipidemic activity) 1 time adm. | | $LD_{50}$ oral (mg/kg) |
|---|---|---|---|---|---|
| | Decrease of cholesterol (mg/dl) | Decrease of triglyceride (mg/dl) | Decrease of cholesterol (mg/dl) | Decrease of triglyceride (mg/dl) | |
| 1 | 126.5 ± 8.1 | 69.7 ± 13.8 | 59.4 ± 4.8 | 52.2 ± 7.6 | 2500 |
| *** | 285.5 ± 25.3 | 80.9 ± 17.8 | 69.0 ± 5.3 | 46.6 ± 7.3 | |
| P-control(a) | 302.4 ± 30.8 | 141.9 ± 11.0 | | | |
| Normal(a) | | | 83.6 ± 6.2 | 62.6 ± 5.6 | |
| 2 | 215.3 ± 6.7 | 88.5 ± 12.3 | | | 1000 |
| 3 | 211.0 ± 5.5 | 81.6 ± 7.3 | 66.6 ± 1.9 | 60.1 ± 2.8 | 1000 |
| 4 | 187.0 ± 18.1 | 88.7 ± 8.9 | 51.9 ± 2.6 | 38.2 ± 2.5 | 2500 |
| 5 | 147.5 ± 8.3 | 90.3 ± 16.8 | 54.5 ± 2.6 | 60.0 ± 4.2 | 3500 |
| 6 | 243.0 ± 6.1 | 89.2 ± 15.6 | | | 1000 |
| 7 | 123.8 ± 9.1 | 52.1 ± 9.0 | 56.4 ± 5.1 | 45.5 ± 5.4 | 2500 |
| 8 | 185.4 ± 7.1 | 75.6 ± 8.3 | | | 1000 |
| 9 | 188.7 ± 18.4 | 58.5 ± 6.7 | 59.1 ± 3.4 | 56.9 ± 6.1 | 3500 |
| 10 | 196.1 ± 13.2 | 73.6 ± 10.0 | | | 3000 |
| 11 | 203.5 ± 12.1 | 89.4 ± 7.7 | | | 700 |
| 12 | 125.3 ± 8.5 | 50.2 ± 7.5 | | | 2500 |
| *** | 258.5 ± 16.0 | 62.5 ± 9.5 | 55.4 ± 3.1 | 46.8 ± 3.5 | 1500 |
| P-control(b) | 260.0 ± 15.5 | 92.0 ± 12.5 | | | |
| Normal(b) | 57.2 ± 3.5 | 37.6 ± 4.8 | 69.3 ± 4.4 | 52.0 ± 4.4 | |

***:ethyl-δ-(p-chlorophenoxy)-isobutylate
P-control: feed containing cholesterol, no medicament.
Normal: cholesterol-free feed: no medicament
(a)comparison with compound 1
(b)comparison with compounds 2-12

The same tests for hypolipidemic activity (lowering of blood lipid level) were carried out by using the reference compounds (IV). The results are shown in Table 4.

Table 4

| Reference Compound | Normal mice 1 time adm. 200 mg/kg | | |
|---|---|---|---|
| | Total cholesterol (%) | Triglyceride (%) | $LD_{50}$ (mg/kg) |
| 1 | 18 | 36 | 1500 |
| 2 | | | |
| 3 | 16 | 19 | 2000 |
| 4 | | | |
| 5 | 21 | 1 | 1500 |
| 6 | | | |
| 7 | 16 | 8 | >10000 |
| 8 | | | |
| 9 | 7 | 35 | |
| 10 | | | |
| 11 | 24 | 52 | 3000 |
| 12 | | | |
| 13 | 27.7 | 41.9 | >2000 |
| 14 | 21 | 2 | |
| 15 | | | |
| 16 | | | |
| 17 | | | |
| 18 | | | |
| 19 | | | |
| 20 | 19 | 7 | >3000 |
| | 15 | 10 | 1500 |

What is claimed is:

1. A benzoyl phenoxy acetic acid derivative having the formula

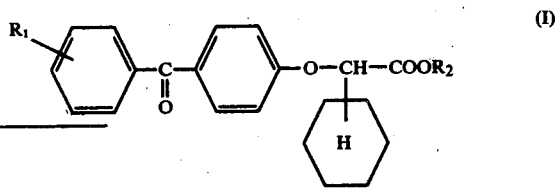

wherein $R_1$ represents a hydrogen or halogen atom, a lower alkyl group, or a lower alkoxyl group; and $R_2$ represents a hydrogen atom or a lower alkyl group.

2. The benzoyl phenoxy acetic acid derivative of claim 1 wherein $R_1$ is a halogen atom.

3. The benzoyl phenoxy acetic acid derivative of claim 1 wherein $R_1$ is Cl.

4. An antihyperlipidemic composition which comprises an antihyperlipidimically effective amount of the benzoyl phenoxy acetic acid having the formula (I) according to claim 1 and a pharmaceutically acceptable carrier.